United States Patent
Blacker et al.

(10) Patent No.: US 11,965,219 B2
(45) Date of Patent: Apr. 23, 2024

(54) PROCESS AND APPARATUS FOR REDUCTION IN MICROBIAL GROWTH IN SOLUTIONS OF SUGARS EXTRACTED FROM WASTE MATERIALS

(71) Applicant: UNIVERSITY OF LEEDS, Leeds (GB)

(72) Inventors: Andrew John Blacker, Leeds (GB); Richard Anthony Bourne, Leeds (GB); William Robert Reynolds, Leeds (GB)

(73) Assignee: UNIVERSITY OF LEEDS, Leeds (GB)

( * ) Notice: Subject to any disclaimer, the term of this patent is extended or adjusted under 35 U.S.C. 154(b) by 740 days.

(21) Appl. No.: 17/055,703

(22) PCT Filed: May 14, 2019

(86) PCT No.: PCT/GB2019/051311
§ 371 (c)(1),
(2) Date: Nov. 16, 2020

(87) PCT Pub. No.: WO2019/220092
PCT Pub. Date: Nov. 21, 2019

(65) Prior Publication Data
US 2021/0207230 A1    Jul. 8, 2021

(30) Foreign Application Priority Data

May 17, 2018    (GB) ..................................... 1807987

(51) Int. Cl.
*C13B 20/00*      (2011.01)
*A01N 43/80*      (2006.01)
(Continued)

(52) U.S. Cl.
CPC ............ *C13B 20/005* (2013.01); *A01N 43/80* (2013.01); *A01N 43/90* (2013.01); *A01N 59/00* (2013.01);
(Continued)

(58) Field of Classification Search
CPC ....... C13B 20/005; C13B 10/12; C13B 50/00; C13B 35/005; A01N 43/80; A01N 43/90;
(Continued)

(56) References Cited

U.S. PATENT DOCUMENTS 5,190,728 A     3/1993   Robertson et al.
9,765,412 B2 *  9/2017   Kurihara .................. C12P 7/56
(Continued)

FOREIGN PATENT DOCUMENTS

CA    2586299 A1 *  5/2006   ............. C12Q 1/10
CA    2722560 C  *  9/2019   ............. A23K 10/00
(Continued)

OTHER PUBLICATIONS

English Translation of Patent Publication JP 3371288, Jan. 2003. (Year: 2003).*
International Search Report and Written Opinion for PCT/GB2019/051311 dated Aug. 13, 2019, 9 pages.

*Primary Examiner* — Joseph W Drodge
(74) *Attorney, Agent, or Firm* — Nixon Peabody LLP; Linda B. Huber

(57) ABSTRACT

A process for reducing microbial growth in solutions of sugars extracted from waste materials, the process comprising monitoring indicators of microbial growth in the solution in situ and administering an antimicrobial; a sugar substrate obtained by concentrating a solution of sugar treated using the process; an apparatus for extracting sugars from waste materials, the apparatus comprising a reaction vessel (10), one or more sensors (15,20) for monitoring indicators of
(Continued)

microbial growth in the reaction vessel, a software for analysing signals from the sensor and a source of antimicrobial.

17 Claims, 4 Drawing Sheets

(51) Int. Cl.
| | | |
|---|---|---|
| *A01N 43/90* | (2006.01) | |
| *A01N 59/00* | (2006.01) | |
| *B01D 11/02* | (2006.01) | |
| *B09B 3/80* | (2022.01) | |
| *C07H 99/00* | (2006.01) | |
| *C12P 19/02* | (2006.01) | |
| *C12Q 1/04* | (2006.01) | |
| *C13B 10/12* | (2011.01) | |
| *C13B 50/00* | (2011.01) | |

(52) U.S. Cl.
CPC ...... *B01D 11/0207* (2013.01); *B01D 11/0288* (2013.01); *B09B 3/80* (2022.01); *C07H 99/00* (2013.01); *C12P 19/02* (2013.01); *C12Q 1/04* (2013.01); *C13B 10/12* (2013.01); *C13B 50/00* (2013.01)

(58) Field of Classification Search
CPC .............. A01N 59/00; B01D 11/0207; B01D 11/0288; B09B 3/80; B09B 5/00; B09B 3/00; C07H 99/00; C12P 19/02; C12P 19/14; C12P 7/10; C12Q 1/04; C12Q 1/02; C12Q 1/06; C12Q 1/18; Y02E 50/10; Y02E 50/30; A23L 3/34; C13K 1/02; C02F 1/008; C02F 1/50; C02F 1/68; C02F 1/685; C02F 1/686; C02F 1/687; C02F 1/76; C02F 1/78; C02F 5/00; C02F 2209/006; C02F 2209/06; C02F 2209/08; C02F 2209/22; C02F 2303/20; G01N 33/1826; G01N 33/48; G01N 33/487; G01N 33/48707
See application file for complete search history.

(56) References Cited

U.S. PATENT DOCUMENTS

| | | | | |
|---|---|---|---|---|
| 11,001,864 | B1* | 5/2021 | Buschmann | C12N 1/18 |
| 11,311,012 | B1* | 4/2022 | Buschmann | A01P 1/00 |
| 2005/0164355 | A1* | 7/2005 | Vlasenko | C12P 7/06 |
| | | | | 435/106 |
| 2014/0148379 | A1* | 5/2014 | Liu | C07K 14/335 |
| | | | | 514/2.4 |
| 2014/0261550 | A1* | 9/2014 | Erickson | C11D 11/0041 |
| | | | | 134/18 |
| 2015/0010958 | A1* | 1/2015 | Huang | C12P 7/10 |
| | | | | 435/141 |
| 2016/0270404 | A1* | 9/2016 | Wichmann | C12P 7/06 |
| 2017/0036928 | A1* | 2/2017 | Kozlowski | C02F 1/001 |
| 2018/0087013 | A1 | 3/2018 | Yu et al. | |
| 2019/0225521 | A1* | 7/2019 | Heath | C02F 1/48 |

FOREIGN PATENT DOCUMENTS

| | | | |
|---|---|---|---|
| JP | 3371288 B2 * | 1/2003 | ................ C02F 1/74 |
| WO | 199726525 A1 | 7/1997 | |
| WO | WO-9726525 A1 * | 7/1997 | ......... G01N 33/1866 |
| WO | 2007149450 A2 | 12/2007 | |
| WO | WO2007145857 A1 * | 12/2007 | ................ C12P 7/06 |
| WO | WO-2007145857 A1 * | 12/2007 | ................ C12P 7/06 |
| WO | 2012066042 A1 | 5/2012 | |
| WO | 2012113042 A1 | 8/2012 | |
| WO | 2015095255 A1 | 6/2015 | |
| WO | WO-2015095255 A1 * | 6/2015 | ................ C12P 7/10 |
| WO | 2019220092 A1 | 11/2019 | |

* cited by examiner

PROCESS AND APPARATUS FOR REDUCTION IN MICROBIAL GROWTH IN SOLUTIONS OF SUGARS EXTRACTED FROM WASTE MATERIALS

CROSS-REFERENCE TO RELATED APPLICATIONS

This application is a National Phase of International Application No. PCT/GB2019/051311, filed May 14, 2019, which designated the U.S. and that International Application was published under PCT Article 21(2) in English. This application also includes a claim of priority under 35 U.S.C. § 119(a) and § 365(b) to British patent application No. GB 1807987.1, filed May 17, 2018, the contents of which are herein incorporated by reference in their entirety.

FIELD

The invention relates to a process for reducing microbial growth in solutions of sugars extracted from waste materials, sugar substrates produced, and to an apparatus for use in such a process.

BACKGROUND

The disposal of municipal waste is a well know problem. Whilst rapid advances have been made in the areas of recycling metals and plastics, the recycling of organic materials has proven to be more problematic. Composting methods are common, as are both anaerobic and aerobic digestion depending upon the nature of the organic waste. Companies such as Fiberight LLC have developed processes for the enzymic digestion of organic materials, such as paper pulp, found in municipal waste to produce solutions of sugars (described in United Kingdom patent application number 1521624.5). These processes typically involve the separation of inorganics and organics in the waste stream before washing the organic material to remove food waste from lignocellulosic material and sterilisation of this lignocellulosic material. The sterilised material is then broken down ("digested") using enzymes to produce sugars which can be removed from solution, purified ("washed") and sold for a variety of uses, including as a fuel. The indigestible material (often known as post-hydrolysis solids) can be dried and is often sold as a fuel.

However, because of the high microbial loading of the municipal waste substrate, an ongoing problem in these processes is microbial growth during the digestion phase. A key problem arising from this is that the microbes can cause the further breakdown of the sugars in to sugar acids such as organic acids, aldonic acids, uronic acids etc. As a result of this breakdown, not only is a valuable commercial product lost in the sugars, but carbon dioxide, a well-known greenhouse gas, is released.

Sterilisation of the organic material prior to digestion is intended to address this problem, but does not completely prevent microbial growth because it does not remove the microbial spores which are resistant to the sterilisation conditions. This makes them very difficult and costly to remove prior to processing. Further, because these processes typically occur in waste processing environments, where the air is inevitably laden with contaminants, there is a risk of airborne contamination after sterilisation. The invention is intended to overcome or ameliorate at least some aspects of this problem.

The control of microbial growth has been considered in unrelated fields, such as in paper manufacture where the level of fouling in the water stream must be controlled to maintain paper quality, and reduce manufacturing down time as a result of the need to clean the apparatus. For instance, U.S. Pat. No. 5,190,728 describes the use of oxygen sensors in the continuous monitoring of microbial growth in water. In the systems of U.S. '728, it is intended to differentiate between chemical and microbiological fouling. This is achieved by promoting microbiological fouling of the sensor through sensor design and the supply of excess oxygen to the system. This results in a system of complexity not needed in the field of the invention, and which may not be robust to the difficulties in analysing viscous opaque solids, such as the sugar solutions produced from the digestion of municipal waste.

SUMMARY

Accordingly, in a first aspect of the invention there is provided a process for reducing microbial growth in solutions of sugars extracted from waste materials, the process comprising:
  a. monitoring indicators of microbial growth in the solution in situ; and
  b. administering an antimicrobial where microbial growth is detected.

A key element of the invention is the ability to monitor the microbial growth in situ. Prior to this point companies working in this field, such as Fiberight, have been unable to monitor microbial growth in the digestion phase without extreme inconvenience. It has been necessary to take samples from the tank and send to a laboratory for analysis. Removal of samples has been hazardous, partly because of the size of the tanks, where simple reaching in to extract a sample is not possible, and partly because of the nature of the solution of sugars. The solution of sugars includes, in addition to the sugars themselves, enzymes, and insoluble post-hydrolysis solids, such that the solution of sugars is a highly viscous, opaque and unpleasant liquid (typically of total solids content in the range 5-40 wt %, often in the range 10-25 wt %). As a result, the solution of sugars would be difficult and messy to sample representatively even if access to the solution were not a concern. In situ monitoring of the microbial growth in the solution removes the need for sample removal from the system. In addition, in many cases the time delay caused by the need to send the sample to a laboratory for analysis renders the results of limited use. This is as microbial growth and sugar production from the enzymic digestion of the organic material result in a solution where the composition is constantly changing. The provision of in situ monitoring of the solution, and the resulting capability for real time analysis, overcomes this problem, and allows the microbial growth to be controlled far faster than was possible before. This reduces the amount of antimicrobial that must be administered and has benefits in terms of a reduction in cost, and in a reduction of contamination of the final sugar product with the antimicrobial, each benefit arising because less antimicrobial is used. In addition, the provision of such accurate monitoring, and rapid response to microbial growth offers the possibility of omitting the expensive and time consuming step of pre-sterilising the organic material prior to enzymic digestion.

As used herein the term "reducing microbial growth" is intended to refer to both the reduction in the growth of the microbes, such that the level of microbial contamination does not further increase; and also to the overall reduction in the level of microbial contamination, such that any colony of microbes shrinks through microbial death. Therefore, it is clear that the antimicrobial may have microbiocidal and/or microbiostatic effects. In many cases, however, the reduction of microbial growth will be the reduction in microbial contamination as a result of a microbiocidal effect of the antimicrobial, such that the solution of sugars is at least partially sterilised. In many cases the object of the process will be to achieve full sterilisation of the solution of sugars, although the reduction in the level of microbial contamination may be such that in the range 80-100% of the microbes present before administration of the antimicrobial, often 90-99.9%, or 95-99.5% of the microbes present before administration of the antimicrobial are killed as a result of sterilisation.

The sugars described are generally extracted using enzymic methods, such as those described above. The sugars will be derived from waste material, such as municipal waste, including domestic, commercial and industrial waste. The sugars present in the solution of sugars will be dependent upon the source of the waste material being processed. As the nature of the organic material in the waste material is highly variable, for instance, as a result of geographic region or time of year, the nature of the sugars produced by digestion of this material is also variable, not only in terms of the type of sugars produced, but also their relative concentration in the solution of sugars. However, the sugars will typically be sugars soluble in water. As a result, the sugars will generally be "simple" sugars, such as mono- and di-saccharides. In many cases at least one of glucose, xylose, or mannose will be present. Where possible disaccharides will be broken down to monosaccharides, and as a result when enzymic digestion is complete, the sugars in the solution of sugars will often comprise mainly glucose and xylose, although arabinose may also be present, as may galactose and mannose.

The process includes the step of monitoring indicators of microbial growth. A wide range of indicators may be used, including carbon dioxide levels, temperature, pH, oxygen levels, lactic acid levels. Often the indicator will be selected from a change in pH and/or a change in dissolved oxygen levels. pH can be used to monitor microbial growth as the presence of microbes increases the acidity of the solution of sugars. Without being bound by theory, it is believed that this is primarily as a result of the formation of lactic acid. Therefore, a drop in pH can be indicative of microbial growth. The indicator of microbial growth may be dissolved oxygen, as microbial respiration causes a reduction in oxygen levels, indicating their presence.

It will often be the case that it is oxygen levels that are monitored, as the oxygen levels can be directly monitored, change rapidly in response to microbial growth and so offer a clear signal that this has occurred, and respond more quickly to microbial growth than a change in pH. This allows for the detection of the microbes when they are at a lower level in the solution of sugars and hence, not only is the breakdown of the sugars into acids minimised, retaining more of the commercially useful sugar product, but also less antimicrobial must be administered. This offers cost savings and reduces contamination of the solution of sugars with the antimicrobial. As pH changes are slower to become apparent, the level of microbes in the solution of sugars is generally higher at the point of detection than when oxygen levels are monitored, and more of the commercially valuable sugar is broken down before administration of the antimicrobial.

Where the indicator of microbial growth is a change in pH, it may be that this is a change in pH by ±2, often a reduction in pH, often by 1.5, or 1, or 0.5. Typically the pH in the absence of microbial growth will be in the range 5-6, as this is the optimal pH for enzymic digestion. Typically, the pH will not fall below 4, sometimes 4.5. Where the indicator of microbial growth is a change in the concentration of dissolved oxygen, the antimicrobial may be administered when a gradient of the decrease of oxygen in the solution of sugars is in the range −0.01 to −0.05 mg/L, often −0.02 to −0.04 mg/L, or in many cases −0.025 to −0.030 mg/L. Where microbial growth is present the concentration of dissolved oxygen can often change from in the range 3-8 mg/L to in the range 0-3 mg/L, often 0.5-2 mg/L or 0 to 1 mg/L or 0.1 to 1 mg/L.

As used herein, the term "microbe" is intended to include any microscopic organism, this may include bacteria, fungi, viruses, protista, archaea, among others. As the nature of the organics in the waste substrate is highly variable, so to can be the nature of the microbial contamination. As such, the microbial growth referred to herein may comprise growth selected from bacterial growth, fungal growth, viral growth, protistal growth, archaeal growth and combinations thereof. Often, however, the microbial growth comprises growth selected from bacterial growth, fungal growth, viral growth, and combinations thereof, as these microbes are generally more prevalent in waste materials. It will generally be the case that bacterial growth will be present, either alone or in combination with other microbial growth types described above.

Where microbial growth is detected, one or more antimicrobials is administered. The nature of the antimicrobial will depend upon the waste substrate and intended end use for the sugars in the solution of sugars and can therefore be selected from a wide range of antimicrobial compounds, compositions and mixtures. For instance, where the purity of the sugars is important, it may be that the antimicrobial selected is one that breaks down, or that is easily removed from the solution of sugars. Also, where toxicity of the antimicrobial to humans or animals may be a concern, the antimicrobial will be selected accordingly. Often the antimicrobial will comprise a microbiocidal component, but microbiostatics can also be used, as can combinations of microbiocidal and microbiostatic components. Often the antimicrobial is selected from antibiotics, disinfectants, antiseptics or combinations thereof. In many cases, the antimicrobial is selected from disinfectants, antiseptics or combinations thereof, as the use of antibiotics can promote antibiotic resistance. As a result, antibiotics will generally be used only where the nature of the microbes present is such that other antimicrobials will not suffice to control microbial growth.

Specific examples of antimicrobial compounds that may be used include, sulphonamide antibiotics, fluoroquinolone antibiotics, streptogramin antibiotics such as virginiamycin, cephalosporings, aminoglycosides, microlides, tetracyclines, alcohols such as ethanol or isopropanol, hexachlorophene, triclosan, chlorooxylenol, chlorhexidine, hydrogen peroxide, ozone, sodium azide, chlorine dioxide, chlorine gas, chloramines, sodium hypochlorite, ethylene oxide gas, formaldehyde, benzisothiazolinone, octylisothiazolinone, dichloro octylisothiazolinone, pyrithione salts such as sodium or zinc pyrithione, silver salts such as silver nitrate, or combinations thereof. Organic acids, such as lactic acid, citric acid or acetic acid and their salts may be used where the indicator of microbial growth is not a change in pH or specific acid concentration. It will often be the case that the antimicrobial will be selected from ozone, silver nanoparticles, sodium azide, benzisothiazolinone, chlorine dioxide and combinations thereof.

To ensure efficacy, whilst minimising the levels of antimicrobials used, it will often be the case that the antimicrobial is administered at levels in the range 0.005-0.015 wt % for sodium azide; $2.5 \times 10^{-4}$–0.05 wt % for BIT; 0.01-0.35 wt % for chlorine dioxide (20% Fermasure™); or 0.002-0.05 wt % for Lactrol. The antimicrobial may be administered in a single dosage, such that there is a single administration in response to each detection of microbial growth, or in multiple aliquots over a period of time after the need for administration is recognised. In addition, it may be that the amount of antimicrobial administered depends upon the level of microbe detected in the solution of sugars, such that detection of a higher level either results in the administration of a single dose containing more antimicrobial or a series of doses, where perhaps only a single dose would be administered where lower levels of microbe are detected. It will therefore be appreciated that the administration of the antimicrobial can be provided in a range of ways, including multiple doses, and differing dosage strengths as described above.

In a second aspect of the invention there is provided sugar substrate obtained by concentrating a solution of sugar treated using the process of the first aspect of the invention. Typically undigested solids will be removed by filtration prior to concentration, in some cases concentration will be such that the solution of sugars will be dried. Concentration may be using any of a range of known techniques, such as concentration of the sugar solution by vacuum distillation, although other methods of concentration may be used.

In a third aspect of the invention there is provided an apparatus for extracting sugars from waste materials, the apparatus comprising:
a. a reaction vessel;
b. one or more sensors for monitoring indicators of microbial growth in the reaction vessel;
c. software for analysing signals from the sensor; and
d. a source of antimicrobial.

As used herein the term "sensor" is intended to refer to any means for providing a signal to the software which allows extrapolation of that signal to an indication of microbial growth. In addition, this term is intended to refer to a single sensor or multiple sensors, which may be present in the apparatus. Where multiple sensors are present they may be the same or different. For instance, multiple oxygen sensors may be present to ensure that monitoring is not interrupted in the event of failure of a single sensor, and to provide for the comparison of signals from more than one sensor to ensure reliability of the readings. Similarly, a combination of sensor types may be present, for instance a combination of pH and oxygen sensors may be present to allow for correlation of signals thereby ensuring that the signals from the sensors are reliable.

The sensor for monitoring indicators of microbial growth will be placed in the reaction vessel, to provide for in situ monitoring of the indicator. The sensor may be placed in the air space above the solution of sugars, and this has the advantage of permitting the use of a wider range of sensors, as direct contact with the solution of sugars introduces problems during sensing because of the highly viscous and opaque nature of the solution. However, the sensors will more often be placed in contact with the solution, as this provides for a more rapid and reliable analysis of the indicators of microbial growth. In particular, where the indicator of microbial growth is a change in pH or dissolved oxygen level, it will generally be the case that the sensor is placed in contact with the solution. Often, where the solution of sugars is mixed, the one or more sensors will be placed at a point within the reaction vessel where the solution of sugars is under the greatest movement. Depending on the mixing method, this may be near to the source of mixing.

Where the indicator of microbial growth is a change in pH and/or a change in oxygen level, the one or more sensors will comprise a sensor selected from a pH sensor and/or an oxygen sensor as appropriate. As it will often be the case that the indicator of microbial growth will be a change in oxygen levels, it will also often be the case that the one or more sensors comprise an oxygen sensor.

A range of sensor designs may be used, however, often the sensor is an electrochemical sensor because electrochemical sensors can be less prone to fouling by the solution of sugars. In particular, some optical sensors have been found to cease operating after only a short period of time due to adherence of the opaque solution of sugar to the sensor preventing further monitoring.

The apparatus will comprise software to analyse signals from the sensor. The presence of software in combination with the sensor provides for in situ monitoring of the microbial growth as described above. This, for the first time, makes it possible to detect microbial levels in real-time and respond rapidly to their increase. The software will generally also control the administering of the antimicrobial in response to signals from the sensor, providing for an automated reaction to increasing microbe levels, ensuring that this is as rapid as possible. Typically this will be effected by providing software which comprises closed-loop feedback control, such that the software can analyse the signals from the sensor and when these detect the indicator of growth to be within certain parameters, the software can also control the administering of the antimicrobial. However, it is possible that the software simply report the result of the analysis to a user, who could manually administer antimicrobial. Where administration is controlled by the software, the apparatus will often additionally comprise an actuator for administering antimicrobial to the reaction vessel.

As described above, administration of the antimicrobial can be in a range of dosage strengths or regimens, and the software will generally be capable of controlling administration in a strength or regimen appropriate in response to the signal received from the sensor.

The reaction vessel, source of antimicrobial and actuator for administering antimicrobial to the reaction vessel used in the apparatus will be typical in this field, and may be of the design used by Fiberight LLC. As will the methods of actuation and mechanical administration of the antimicrobial.

There is therefore provided a process for reducing bacterial, fungal and/or viral growth in solutions of sugars extracted from waste materials, the process comprising:
a. monitoring a reduction in pH or dissolved oxygen levels where a gradient of the decrease of oxygen in the solution of sugars is in the range −0.025 to −0.030 in the solution in situ; and
b. administering an antimicrobial selected from disinfectants, antiseptics, or combinations thereof, where bacterial, fungal and/or viral growth is detected. Often the antimicrobial will be selected from ozone, sodium azide, chlorine dioxide, benzisothiazolinone or combinations thereof.

Also provided is an apparatus for extracting sugars from waste materials, the apparatus comprising:
a. a reaction vessel;

b. one or more electrochemical pH and/or oxygen sensors in contact with the a solution of sugars in the reaction vessel;
c. closed-loop feedback control software for analysing signals from the sensor and controlling administration of the antimicrobial in response to signals from the sensor;
d. a source of antimicrobial; and
e. an actuator for administering antimicrobial to the reaction vessel.

Unless otherwise stated each of the integers described may be used in combination with any other integer as would be understood by the person skilled in the art. Further, although all aspects of the invention preferably "comprise" the features described in relation to that aspect, it is specifically envisaged that they may "consist" or "consist essentially" of those features outlined in the claims. In addition, all terms, unless specifically defined herein, are intended to be given their commonly understood meaning in the art.

Further, in the discussion of the invention, unless stated to the contrary, the disclosure of alternative values for the upper or lower limit of the permitted range of a parameter, is to be construed as an implied statement that each intermediate value of said parameter, lying between the smaller and greater of the alternatives, is itself also disclosed as a possible value for the parameter.

In addition, unless otherwise stated, all numerical values appearing in this application are to be understood as being modified by the term "about".

BRIEF DESCRIPTION OF THE DRAWINGS

In order that the invention may be more readily understood, it will be described further with reference to the figures and to the specific examples hereinafter.

DETAILED DESCRIPTION

Figure 1:
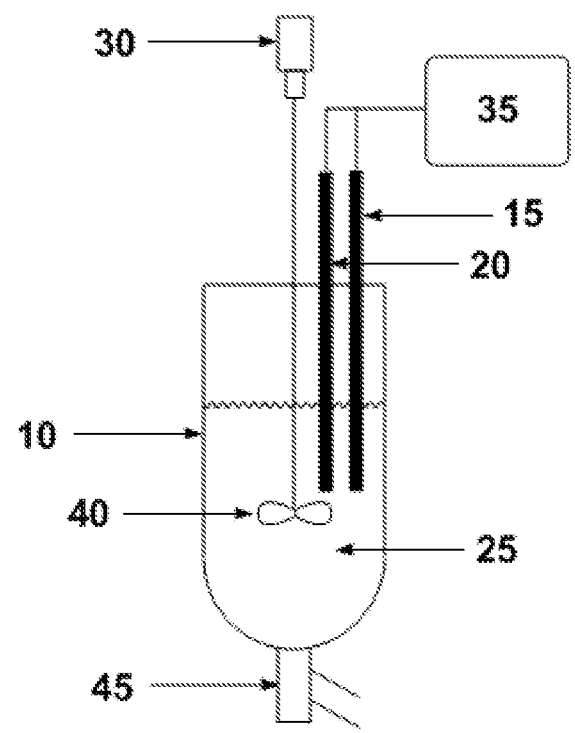
FIG. 1 is a schematic representation of an apparatus of the invention.

The apparatus 5 of the invention is shown in FIG. 1. The apparatus comprises reaction vessel 10, a pH sensor 15, oxygen sensor 20 and a source of antimicrobial (not shown).

In this example, stirring of the solution of sugars 25 is provided for using an agitator, the agitator comprising an agitator motor 30 and agitator blades 40. The pH 15 and oxygen 20 sensors send signals to a control unit 35, which analyses those signals and controls the administration of antimicrobial. Once enzymic digestion of the organic substrate is complete, the solution of sugars 25 can be released from the reaction vessel 10 through outlet 45.

EXAMPLES

Process Procedure—Single Solids Addition (1 Litre Reaction Vessel)

The process described is based upon the Fiberight industrial scale process, modified for a 1 litre reaction vessel. The amount of organic substrate used in the process is dependent on the required total solids (TS) content of the process. Typically, TS will be between 5-25%. TS is calculated using the required reaction mass and the solids content of the organic substrate, which is typically between 10-70%. (For a reaction mass of 1 kg, with a required TS of 8% (w/w), using organic substrate with a solids content of 32% (w/w), the amount of organic substrate needed for the process is 250 g). The organic substrate is sterilised in an autoclave at 125° C. for 1 hour immediately prior to use.

The reaction vessel is sterilised prior to use by filling with sodium hydroxide and stirring for 1 hour. The ethanol is then drained and the heating jacket set to 50° C. prior to addition of the reaction components (water, organic substrate, and enzyme).

The organic substrate is added to a preheated reaction vessel (50° C.) in one portion followed by sterilised water (the mass of water required=total reaction mass−mass of organic substrate) and stirred at between 200-600 RPM, depending on TS (higher TS requires a higher RPM to ensure thorough mixing). The pH, and dissolved oxygen (DO) sensors are each inserted into the reaction mixture (solution of sugars) at the top of the reaction vessel and positioned so that the tips are within a mixing zone created by the presence of an agitator, typically 20-30 mm above the agitator blades. The sensors are turned on and measurements initiated. If the pH of the reaction is below 5 then ammonium hydroxide is added in small portions until the pH is between 5 and 6. The required amount of enzyme, typically between 0.5-3% (w/w) of the TS, is then added to the reaction vessel. The point at which the enzyme is added is the start of the process (T=0 hours). Throughout the process pH is maintained between 5-6 (with the addition of an alkali agent as required). DO readings are taken throughout the process and are typically between 3-8 mg/L if no contamination is present. Between T=0-3 hours DO readings are not constant and can vary significantly, due to changes in the viscosity of the process as the enzyme breaks down the organic substrate. Typically this stops after T=3 hours and maintains linear readings. If contamination occurs the DO reading can drop to 0 mg/L, which typically happens between T=5-8 hours. The end of the process is typically between T=90-110 hours, when no further increase in sugar concentration is observed. For TS between 5-20%, final sugar concentrations will typically be between 30-100 g/L.

At the end of the process the reaction vessel is drained and the reaction mixture is filtered under vacuum to separate the residual post-hydrolysis solids (PHS) from the sugar solution. The sugar solution is then concentrated by vacuum distillation to the required concentration for use.

Process Procedure—Multiple Solids Addition (10 Litre Reaction Vessel)

The process described is based upon the Fiberight industrial scale process, modified for a 10 litre reaction vessel. The single solids addition procedure outlined above becomes difficult to use for TS>10% because the reaction vessel contents do not mix sufficiently. To address this, a multiple solids addition strategy is used. In this example, the multiple solids addition strategy is conducted in a reaction vessel volume of >10 litres. The required mass of organic substrate is separated into 6-8 portions. The first two portions are added to the reaction vessel according the procedure outlined above (T=0 hours). The remaining 4-6 portions are added to the reaction vessel one at a time at T=9, 18, 27, 36 hours if four portions and additionally at T=45, 54 hours if five or six portions. After the final portion of organic substrate has been added the procedure outlined above is followed to completion.

Microbial Contamination Control Procedure

Several sterilisation agents have been tested to determine their effectiveness in controlling microbial growth in solutions of sugar. The sterilisation agents were either introduced at T=0 or at the point that microbial growth is observed, which can be measured by the DO sensor. Typically, contamination can be said to occur when the DO reading starts to drop exponentially, eventually reaching 0 mg/L if no sterilisation agent is added. In these tests, software was used to monitor the DO readings and trigger the addition of an antimicrobial. Typically this happens when the gradient of the decrease is in the range −0.025 and −0.030. Once a sterilisation agent has been added the DO readings will start to increase within 5-10 minutes.

Figure 2:
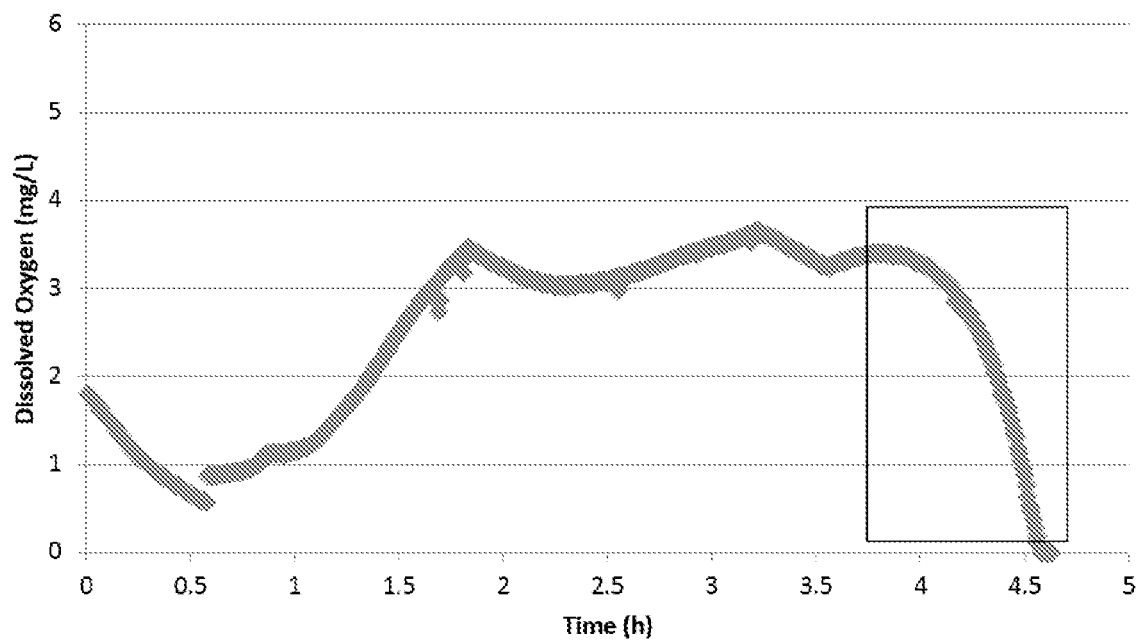
FIG. 2 is a graph illustrating the dissolved oxygen response of a solution of sugars over time with no microbial control. The area in the rectangle shows the onset of microbial growth.

The results are illustrated in FIGS. 2-7. In these figures, FIG. 2 is a control example, where microbial growth is allowed to proceed without intervention. As can be seen, the oxygen content of the solution of sugars drops markedly in the period 4-4.5 hours, indicating the onset of microbial growth.

Figure 3:
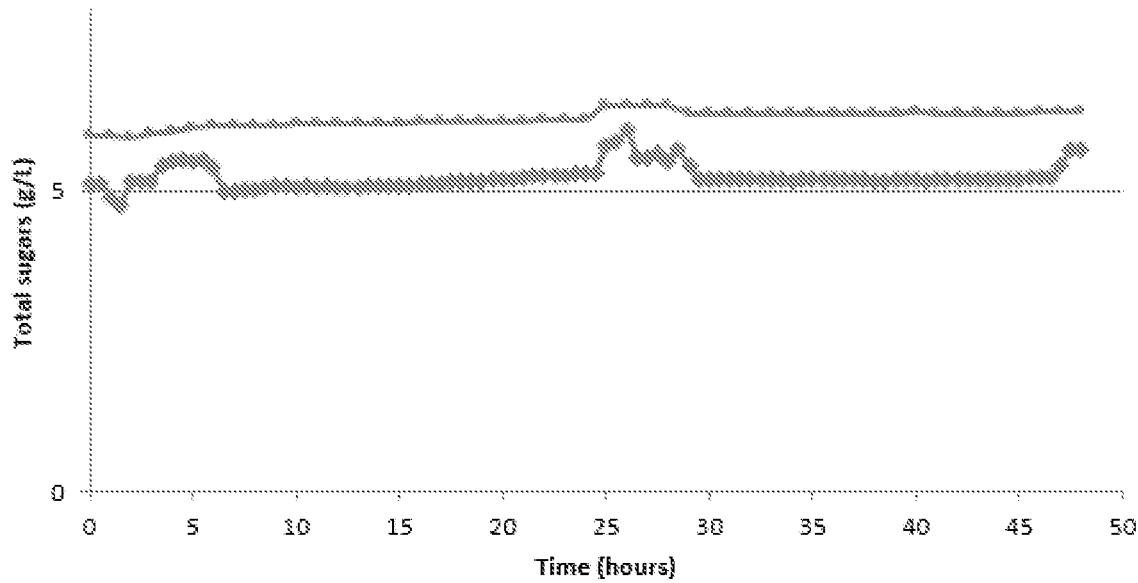
FIG. 3 is a graph illustrating the dissolved oxygen (lower line) and pH (upper line) responses of a solution of sugars over time with the addition of sodium azide at T=0.
Figure 4:
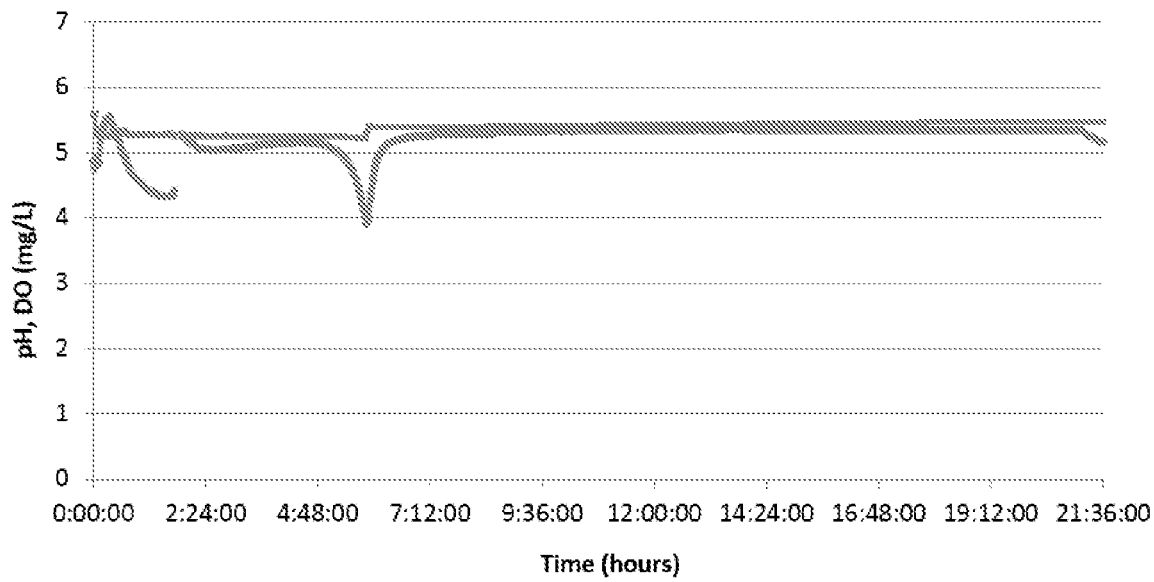
FIG. 4 is a graph illustrating the dissolved oxygen (lower line) and pH (upper line) responses of a solution of sugars over time with the addition of sodium azide at T=5 hrs 45 mins.

FIGS. 3 and 4 show the addition of sodium azide, in FIG. 3 at T=0, and in FIG. 4, in response to a drop in the levels of dissolved oxygen in the sugar solution, at T=5 hrs 45 mins. As can be seen, the addition of sodium azide at T=0 results in stable pH and oxygen levels throughout the test, indicating an absence of microbial growth. However, this can also be achieved, through the monitoring of pH and/or oxygen levels and, as shown in FIG. 4, the addition of sodium azide only when needed. In this case, at around 5 hr 45 minutes when both the level of dissolved oxygen and the pH drop. This provides a solution of sugars which is apparently free from microbial growth for the remainder of the test, and shows that the addition of sodium azide is capable of preventing microbial growth for the duration of the test, whether added initially or later in the process.

Figure 5:
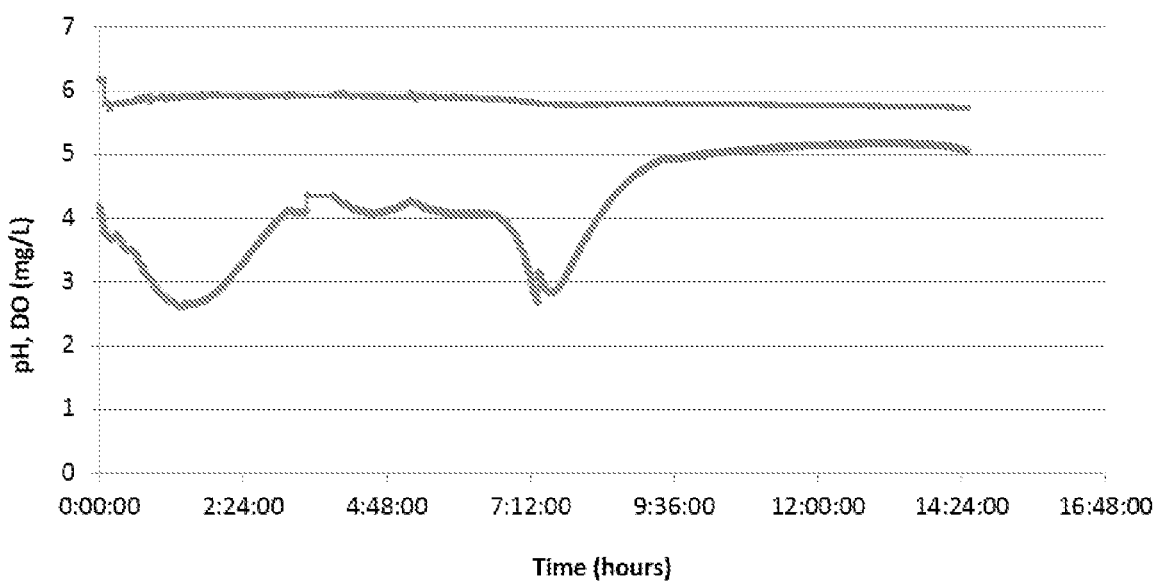
FIG. 5 is a graph illustrating the dissolved oxygen (lower line) and pH (upper line) responses of a solution of sugars over time with the addition of lactrol at T=7 hrs.

FIG. 5 shows a test where the antibiotic lactrol was added to the solution of sugars at T=7 hrs, directly in response to an observed drop in dissolved oxygen and pH. The result was the stabilisation of these parameters for the duration of the test.

Figure 6:
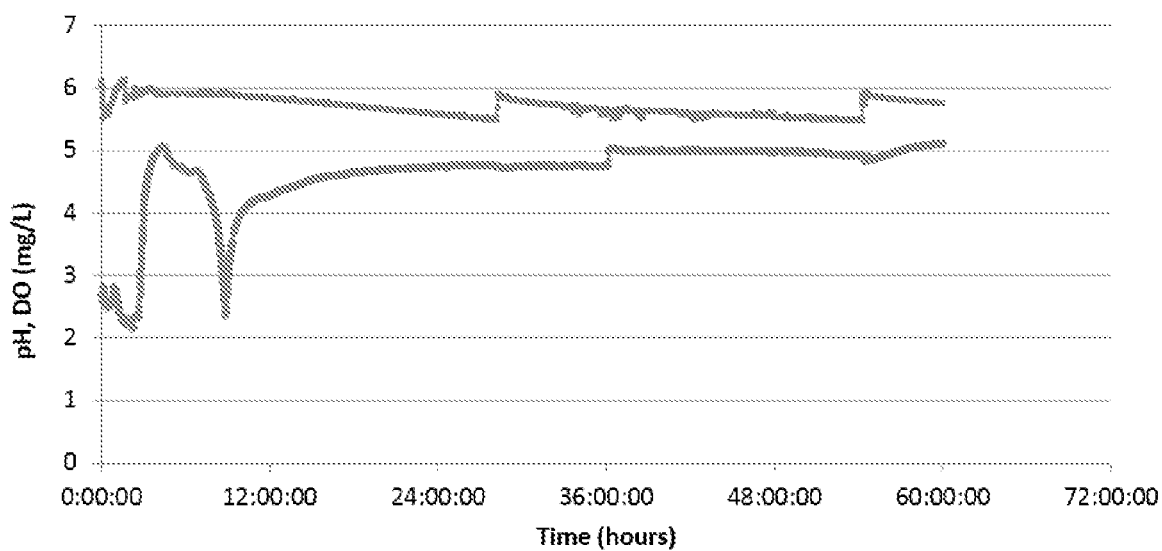
FIG. 6 is a graph illustrating the dissolved oxygen (lower line) and pH (upper line) responses of a solution of sugars over time with the addition of chlorine dioxide (0.35 wt % Fermasure™) at T=8 hrs 45 mins.
Figure 7:
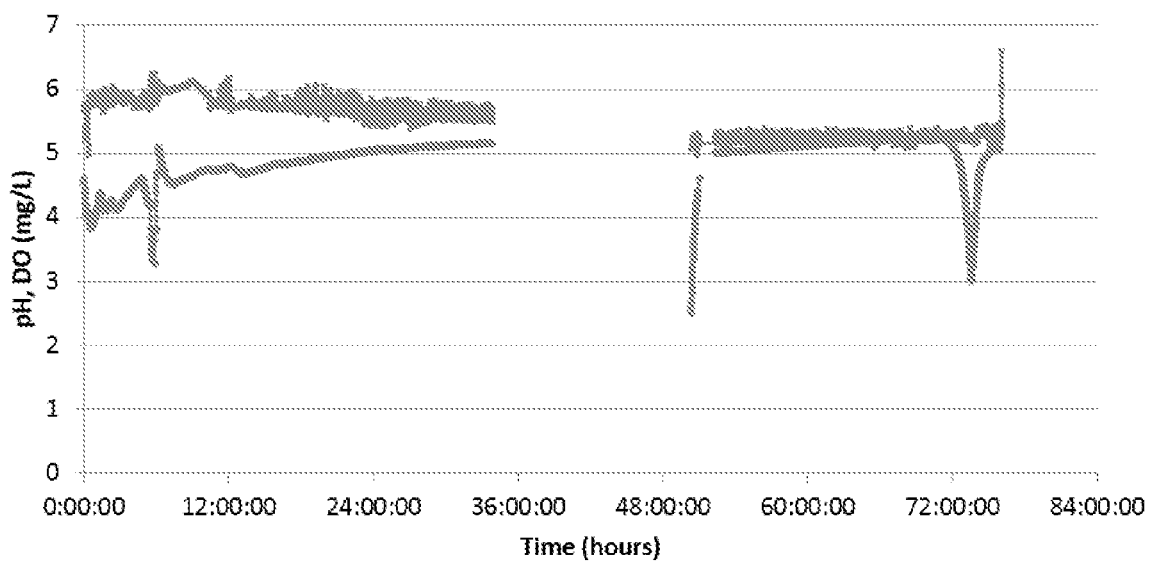
FIG. 7 is a graph illustrating the dissolved oxygen (lower line) and pH (upper line) responses of a solution of sugars over time with the addition of chlorine dioxide (0.05 wt % Fermasure™) at T=5 hrs 45 mins, T=50 hrs 30 mins and T=73 hrs 30 mins. Data missing for time period 36-50 hours, but expected to follow the trend of the Figure as a whole.

FIGS. 6 and 7 show systems where chlorine dioxide (Fermasure™) was used to stabilise dissolved oxygen and pH levels, thereby preventing further microbial growth. In these figures, pH drop is less marked as chlorine dioxide was added in response to the drop in dissolved oxygen. As the drop in dissolved oxygen occurs before the pH drop, pH drop (evidence of lactic acid production) was prevented. In FIG. 6, 0.35 wt % chlorine dioxide was added at T=8 hrs 45 mins in a single aliquot, in FIG. 7 a lower concentration of chlorine dioxide, 0.05 wt %, was added at T=5 hrs 45 mins, T=50 hrs 30 mins and T=73 hrs 30 mins in response to recurrent microbial growth instances, as indicated by a reduction in pH and dissolved oxygen. A comparison of the tests of FIGS. 6 and 7 shows that a reduction in total antimicrobial used can be achieved using the process of the invention. This is because repeated dosing of the solution of sugars can be achieved with lower concentrations of antimicrobial, hence, even though several additions are required, less of the active is needed to control microbial levels. This provides cost savings and reduces the environmental impact of the process claimed.

It has therefore been shown that a wide range of antimicrobials can be used to control the microbial growth in the solutions of sugars. Further, it is clear that both pH and oxygen levels can be used as an indicator of microbial growth, as both pH and oxygen levels return to previous levels after addition of the antimicrobial.

It should be appreciated that the processes and apparatus of the invention are capable of being implemented in a variety of ways, only a few of which have been illustrated and described above.

The invention claimed is:

1. A process for reducing microbial growth in a solution of sugars extracted from waste materials, the process comprising:
   a. monitoring one or more indicators of microbial growth in the solution in situ; and
   b. administering one or more antimicrobials in response to microbial growth being detected based on the one or more indicators of microbial growth,
   wherein the one or more indicators of microbial growth comprise dissolved oxygen.

2. A process according to claim 1, wherein the one or more indicators of microbial growth further comprises pH.

3. A process according to claim 1, wherein the one or more indicators of microbial growth is a concentration of dissolved oxygen in a range of 0-1 mg/L.

4. A process according to claim 1, wherein the microbial growth is growth selected from bacterial growth, fungal growth, viral growth, protistal growth, archaeal growth and combinations thereof.

5. A process according to claim 4, wherein the microbial growth is growth selected from bacterial growth, fungal growth, viral growth, and combinations thereof.

6. A process according to claim 1, wherein the one or more antimicrobials are selected from antibiotics, disinfectants, antiseptics or combinations thereof.

7. A process according to claim 6, wherein the one or more antimicrobials are selected from disinfectants, antiseptics or combinations thereof.

8. A process according to claim 1, wherein the one or more antimicrobials are selected from ozone, sodium azide, chlorine dioxide, benzisothiazolinone (BIT) or combinations thereof.

9. A process according to claim 8, wherein the one or more antimicrobials are administered at levels in a range of 0.005-0.015 wt % for sodium azide; $2.5 \times 10^{-4}$-0.05 wt % for BIT; 0.01-0.35 wt % for chlorine dioxide or 0.002-0.05 wt % for virginiamycin.

10. A process according to claim 1, wherein the one or more antimicrobials are administered when a gradient of a decrease of oxygen in the solution of sugars is in the range −0.025 to −0.030 mg/L.

11. An apparatus for extracting sugars from waste materials, the apparatus comprising:
   a. a reaction vessel;
   b. one or more sensors for monitoring one or more indicators of microbial growth in the reaction vessel, wherein the one or more indicators of microbial growth comprises dissolved oxygen;
   c. software for analysing signals from the one or more sensors and controlling administering of an antimicrobial in response to signals from the one or more sensors; and
   d. a source of the antimicrobial.

12. An apparatus according to claim 11, wherein the one or more sensors are in contact with a solution of sugar extracted from waste materials.

13. An apparatus according to claim 11, wherein the one or more sensors comprise one or more sensors selected from a pH sensor and/or an oxygen sensor.

14. An apparatus according to claim 11, wherein the one or more sensors comprise an oxygen sensor.

15. An apparatus according to claim 11, wherein the one or more sensors comprise an electrochemical sensor.

16. An apparatus according to claim 11, wherein the software comprises closed-loop feedback control software.

17. An apparatus according to claim 11, further comprising an actuator for administering the antimicrobial to the reaction vessel.

* * * * *